United States Patent [19]

Itil

[11] 4,096,266

[45] Jun. 20, 1978

[54] LISURIDE IN ALCOHOLISM

[75] Inventor: Turan M. Itil, Tarrytown, N.Y.

[73] Assignee: HZI Research Center, Tarrytown, N.Y.

[21] Appl. No.: 674,217

[22] Filed: Apr. 6, 1976

[51] Int. Cl.² ............................................. A61K 31/48
[52] U.S. Cl. ................................................... 424/261
[58] Field of Search ........................................ 424/261

[56] References Cited

U.S. PATENT DOCUMENTS

| 3,681,497 | 8/1972 | Semonsky et al. ................... 424/261 |
| 3,953,454 | 4/1976 | Zikan et al. ........................... 424/261 |
| 3,954,988 | 5/1976 | Itil ......................................... 424/261 |

*Primary Examiner*—Sam Rosen

[57] ABSTRACT

Lisuride can be administered to persons prior or subsequent to the ingestion of alcohol to block the behavioral and physiological effects of the alcohol.

10 Claims, No Drawings

LISURIDE IN ALCOHOLISM

This invention relates to a new use for Lisuride, and particularly relates to the effects of Lisuride on alcoholism.

Lisuridehydrogen maleate (N-D-6-methyl-8-isoergolenyl-Nl, Nl-diethyl-urea as hydrogen maleate), a derivative of isolysergide acid having the following formula

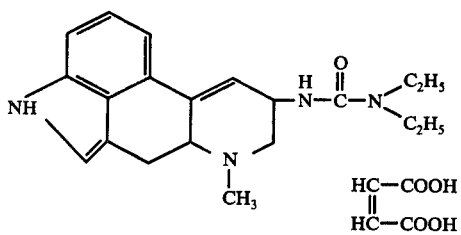

was synthesized by Zikan and Semonsky (Zikan, V., M. Semonsky: Coll. Czech. Chem. Commun. (1960), 1922) in order to develop an LSD-25 analog with antiserotonin and antihistamine properties without having hallucinogenic side effects. The pharmacological investigations confirmed the antiserotonin and antihistamine properties of Lisuride (Podvalova, I., Z. Votava: Archives of the Res. Inst. Pharm. Biochem., Prague 1965).

In one of the first clinical trials, Vojtechovsky et al (Activ. Nerv. Super. 5 (1963), 211) found in about half of the cases a moderate inhibitive dysphoric effect, while in about one third they found a slight central nervous system (CNS) effect without autonomous symptoms. In half of the subjects, however, the changes were so slight that they could not be distinguished from placebo. Lisuride did not alter the mental functions in psychological tests. The effects of methysergide seemed to be more intense, so that it could be distinguished from placebo in 80% of the cases. Both Lisuride and methysergide reduced paroxysmal discharges of high voltage slow waves occurring after hyperventilation, with an acceleration of waves in electroencephalogram (EEG).

The study of Votava and Lamplova (Therapy Vol. 19 (1964), 733–742) showed that autonomic effects were similar for LSD and methysergide and weaker for LHM, but in higher dosages Lisuride approached the others. Lisuride has been found to have "neither hallucinogenic nor central actions".

A series of investigations reported favorable results in patients with migrainous cephalalgia (Vrcha, L.: Archives of the Res. Inst. Pharm. Bilchem., Prague 1965) (Bohanes, M.Q.: Farmakoterp. Zpravy Spofa 13 (1967)) (Novotny, S., V. Gall.: Farmakoterap. Zpravy. Spofa 13 (1967)).

Systematic clinical double-blind trials compared with placebo and methysergide have proven the effectiveness of LHM in migraine headache.

Lisuride was also tried on other diseases in which serotonin was supposed to play an important role, for example, in allergic diseases and post-resection syndrome. In allergic diseases such as urticaria, Quincke's edema, eczema, etc., Lisuride showed good results as reported by Rozsivalova and Dlabalova (Archives of the Res. Inst. Pharm. Bilchem., Prague 1966) and Paskova et al. (Archives of the Res. Inst. Biochem., Prague 1965). A peripheral antiserotonin effect of Lisuride was shown in two patients with malignant carcinoid syndrome by Kojecky and Smoldas (Archives of the Res. Inst. Pharm. Biochem., Prague 1965).

Itil et al (Int. J. Clin. Pharmacol. (1975), pages 221–223) using "Quantitative pharmaco-EEG" techniques developed by Itil in a series of studies have found that lisuridehydrogen maleate produces systematic changes in computerized EEG measurement. The computer EEG (CEEG) profile of Lisuride showed some similarities to those seen after administration of psychostimulant compounds. In lesser degree, it also resembles anxiolytic drugs. Based on the CEEG profiles, a series of clinical applications of Lisuride was predicted. A new application of Lisuride, administered orally, is the possibility of the blocking of the clinical and physiological effects of alcohol. The predictions that Lisuride should have therapeutic potentials in patients with "aging" and/or organic brain syndromes, in children with behavioral disturbances were supported by clinical pilot trials. A recent unpublished double-blind controlled study demonstrated the therapeutic effects of Lisuride on psycho-physiological disorders ("Neurasthenia").

According to this invention Lisuride is administered to a subject prior or subsequent to the ingestion of alcohol in an amount effective to block the CNS effects of the alcohol, i.e., the Lisuride serves as a blocking agent for alcohol intoxication.

Based on investigations carried out with normal healthy volunteers as subjects, it was established that computer EEG profiles induced by alcohol are altered with prior or subsequent treatment of Lisuride. In different recordings (during Resting or Reaction time) at different time periods (1 hr. or 3 hrs., the changes induced by alcohol in more than half of the CEEG measurements were modified in completely opposite directions after pretreatment with Lisuride compared with pretreatment with placebo.

The results of the investigations established that Lisuride has blocking effects on the CNS effects of alcohol, justifying the conclusion that Lisuride functions as a blocking agent for alcohol intoxication.

The following examples are given in order to illustrate the invention but are in no way to be construed as a limitation of the scope thereof.

EXAMPLE I

MATERIAL AND METHOD

A. Demographic Data

Three psychologically and physically healthy, white, male volunteers (all semi-skilled; two single and one married) in the age range of 22–28 years (mean 24.3 years) were included in this study.

B. Method

Each subject was given 100 cc of 80 proof (40% alcohol) vodka in orange juice. Subjects drank the mixture within 15 minutes. Two hours before alcohol administration, subjects received, randomly, one single dose of 50 mcg Lisuride or placebo orally. EEG recordings, sedation, and psychosomatic rating scales were done before and 1 hour and 3 hours after Lisuride or placebo administration (the latter 1 hour after alcohol administration). During each recording two 5 minute EEG recordings were done (5 minute resting recording and five minute reaction time recording). Right occipital to right ear and anterior vertex to right occipital leads were also recorded on tape and later analyzed using IBM System 7.

C. RESULTS

(a) Clinical Results

Clinical findings were established based on the Psychosomatic Rating Scale and the Self-Rating Scale for Sedative and Tranquilizant Drugs.

1. Lisuride (50 mcg.) and Alcohol (All at 3rd Hour):
   Blurred vision — slight, one subject (#3)
   Burning sensation in stomach — slight, one subject (#2)
   Burning sensation in hands, etc. — slight, one subject (#3)
   Drowsiness — slight, one subject (#3); marked, one subject (#2)
   Sleepy — slight, one subject (#2)
   Increased perspiration — moderate, one subject (#2)
   Weakness — slight, one subject (#3)
   Dizziness — moderate, one subject (#1)
   Drunkeness — slight, one subject (#3); moderate, one subject (#1)
   Euphoria — slight, three subjects (#1, 2, 3)
   Heavy headedness — moderate, one subject (#2)
   Relaxation — slight, one subject (#3)
   Flushing — marked, one subject (#2)

2. Placebo and Alcohol (All at 3rd Hour):
   Drowsiness — slight, one subject (#3); moderate, one subject (#1)
   Increased perspiration — moderate, one subject (#2)
   Drunkeness — slight, one subject (#1)
   Euphoria — marked, one subject (#2)
   Happy — slight, one subject (#2)
   Flushing — marked, one subject (#2)

Euphoria was seen in all three subjects after the Lisuride and alcohol combination, while only in one subject was this observed after the placebo and alcohol combination.

Table I which follows shows the population data of the study.

Table I

| Initials | Age | Sex | Race | Occupation | Marital Status | Present Status |
|---|---|---|---|---|---|---|
| N.O. | 23 | M | W | Semi/Skill | Single | Normal Volunt. |
| Z.I. | 28 | M | W | Semi/Skill | Married | Normal Volunt. |
| E.U. | 22 | M | W | Semi/Skill | Single | Normal Volunt. |

Age range: 22-28  3 normal white male volunteers  2 single vol.
Age mean: 24.3  3 semi-skilled volunteers  1 married vol.

The following results were observed in individual subjects.

| | |
|---|---|
| Patient's study No.: | 1 |
| Patient's initials: | N.O. |
| Age: | 23 |
| Sex: | M |
| Race: | W |
| Diagnosis: | Normal Volunteer |
| Length of treatment: | 3/4/75–3/13/75 |
| Sex: | M |
| Race: | W |
| Diagnosis: | Normal Volunteer |
| Length of treatment: | 3/4/75–1/13/75 |
| Total Dosage: | 50 mcg lisuride, placebo, 100 cc alcohol 80 proof (40% alcohol) in fruit juice |
| Clinical side effects: | With 50 mcg lisuride and alcohol: dizziness, drunkeness, euphoria at the 3rd hour. Placebo and alcohol: drowsiness, drunkeness at the 3rd hour. |
| Overall Summary: | The side effects that occurred during this study were: Dizziness: moderately, with 50 mcg lisuride and alcohol at the 3rd hour. Drunkeness: moderately, with 50 mcg lisuride and alcohol, and slightly with placebo and alcohol at the 3rd hour. Euphoria: slight, with 50 mcg lisuride and alcohol at the 3rd hour. Drowsiness: moderately, with 50 mcg. lisuride and alcohol at 3rd hour. |

| | |
|---|---|
| Patient's study No.: | 2 |
| Patient's initials: | Z.I. |
| Age: | 28 |
| Sex: | M |
| Race: | W |
| Diagnosis: | Normal Volunteer |
| Length of treatment: | 3.13.75 – 3.20.75 |
| Total dosage: | Lisuride 50 mcg Placebo Alcohol 40% (100 cc Vodka, 80 proof, in fruit juice) |
| Clinical side effects: | With: 50 mcg Lisuride and alcohol: euphoria, burning sensation in stomach, sleepiness, increased perspiration, heavy headedness, drowsiness, and flushing at 3rd hour. Placebo and alochol: Happiness, relaxation, increased perspiration, euphorea at the 3rd hour. |
| Overall summary: | The side effects that have occurred were: Euphoria: slightly Lisuride lisuride 50 mcg markedly with placebo and alcohol and markedly with placebo and alcohol at 3rd hour. Burning sensation in stomach: slightly with 50 mcg lisuride and alcohol at the 3rd hour. Sleepiness: slightly with 50 mcg Lisuride and alcohol at the 3rd hour. Increased perspiration: moderately with 50 mcg Lisuride and alcohol with placebo and alcohol at 3rd hour. Heavy headedness: moderately with 50 mcg Lisuride and alcohol at the 3rd hour. Drowsiness: markedly with 50 mcg Lisuride and alcohol at the 3rd hour. Happiness and relaxation: slightly with placebo and alcohol at the 3rd hour. Flushing: markedly with Lisuride 50 mcg and alcohol at the 3rd hour. |

| | |
|---|---|
| Patient's study No.: | 3 |
| Patient's initials: | E.U. |
| Age: | 22 |
| Sex: | M |
| Race: | W |
| Diagnosis: | Normal Volunteer |
| Length of treatment: | 3.13.1975 – 3.20.1975 |
| Total dosage: | Lisuride 50 mcg Placebo Alcohol 40% (100 cc Vodka, 80 proof, in fruit juice) |
| Clinical side effects: | With: 50 mcg Lisuride and alcohol: blurred vision, burning sensation in the body, drowsiness, weakness, drunkeness, euphoria relaxation at 3rd hour. Placebo and alcohol: drowsiness, relaxation. |
| Overall summary: | The side effects that occurred were: Blurred vision: slightly with 50 mcg Lisuride and alcohol. Burning sensation in the body: slightly with 50 mcg Lisuride and alcohol at 3rd hour. Drowsiness and relaxation: slightly with 50 mcg Lisuride and alcohol and placebo and alcohol at the 3rd hour. Weakness, drunkeness and euphoria: |

-continued slightly with 50 mcg Lisuride and alcohol at the 3rd hour.

COMPUTER EEG FINDINGS

As described above, a 10-minute EEG recording (5 minutes during resting and 5 minutes during reaction time measurements) was done on each subject before placebo or Lisuride administration, one hour after alcohol administration (2 hours after placebo or Lisuride), and 3 hours after alcohol administration (4 hours after placebo or Lisuride administration). The changes from pre-drug (Lisuride or placebo) to 1 hour and 3 hours after alcohol (2 hours and 4 hours after Lisuride or placebo) was demonstrated in terms of t-values for each individual subject, as well as for the group, for the resting and reaction time recordings.

1. CEEG PROFILES OF INDIVIDUAL SUBJECTS a. Subject #1

Placebo plus alcohol-induced changes in this subject during resting recordings were only slightly different than those seen after Lisuride and alcohol-induced changes. During reaction time recording suggesting however Lisuride produced a slight degree of blocking effects on alcohol-induced CEEG changes.

b. Subject #2

During resting, but particularly during reaction time recordings, the changes induced after placebo/alcohol were different than those seen after Lisuride/alcohol. Lisuride did reverse in moderate to marked degree the changes induced by alcohol.

c. Subject #3

During both resting and reaction time recordings the changes induced by placebo/alcohol were markedly reversed during recordings after Lisuride/alcohol.

It is interesting that both subjects #2 and #3 who showed reverse physiological effects of alcohol after pretreatment with Lisuride had predominantly alpha records, whereas subject #1, who did show only slight reversal effects of alcohol by Lisuride, had less alpha waves and more slow and fast activities.

2. GROUP CEEG PROFILES

During the resting recording, except in the first derivative measurement, no predominant and/or systematic changes were observed after alcohol (placebo pretreatment). However, during both the 1- and 3- hour recordings, 13 of 22 CEEG measurements showed changes in different directions after pretreatment with Lisuride compared to the recordings after pretreatment with placebo. After placebo/alcohol the decrease in 26.6–40 cps activity reached the level of statistical significance while after Lisuride/alcohol the increase of average amplitude reached the level of statistical significance (only at 3 hours).

During reaction time recordings the alcohol-induced changes were characterized by an increase of 7.5–13 cps waves, a decrease of very slow waves and 26.6–40 cps activities in the primary wave measurements, and an increase of activities above 50 cps and a decrease of activities in the 20–50 cps range in the first derivative measurements. Three hours after alcohol the increase of 7.5–13 cps activity and a decrease of primary wave average frequency reached the level of statistical significance. Thirteen of 22 measurements during the first hour recording and 12 of 22 CEEG measurements during the third hour recording showed changes in opposite directions after placebo/alcohol and Lisuride/alcohol. This suggests, again, that the pretreatment with Lisuride did indeed reverse the quantity and quality of CEEG changes induced by alcohol.

According to this study, alcohol produced in one subject (#1) a psychostimulant-type CEEG profile, while subject #2 (third hour RT) showed a novel CEEG profile (alcohol CEEG profile). A summary of the computer EEG Individual Drug Profiles can be seen from Table I which is set out below. The group CEEG profile during the reaction time recordings was similar to that of subjects #2 and #3, namely a novel profile. In all three subjects, as well as in a group, in both time periods (1 hour and 3 hours) and during both recordings (RR and RT), the blocking effect of Lisuride on the alcohol-induced CEEG profiles was observed (except subject #1's RR recordings). The marked blocking effect was seen during reaction time recordings in subjects #2 and #3 as well as in the group.

This study is strongly suggestive that Lisuride, 3 hours after 50 mcg. oral administration, produced reversal effects of the changes induced by alcohol (100 cc 80 proof Vodka; 40% alcohol). These findings support the prediction which was made based on the previous Lisuride studies.

Table I

| DRUG SUBJECTS | PERIOD | PLACEBO AND ALCOHOL 1 HR | PLACEBO AND ALCOHOL 3 HR | LISURIDE AND ALCOHOL 1 HR | LISURIDE AND ALCOHOL 3 HR |
|---|---|---|---|---|---|
| SUBJECT 1 | RR | P | P | P | P |
|  | RT | P | P | P / B+ | P / B+ |
| SUBJECT 2 | RR |  |  | B++ | B++ |
|  | RT |  | X | B+++ | B+++ |
| SUBJECT 3 | RR |  |  | B+++ | B+++ |
|  | RT | X | X | X | X |
| GROUP PROFILE (N:3) | RR |  |  | B+ | B+ |
|  | RT | X | X | B+++ | B+++ |

CODE:
+ Slight
++ Moderate
+++ Marked
P = Psychostimulant
X = New Profile (Alcohol)
B = Blocking effects of Lisuride on Alcohol CEEG Profile In the first aspect of the invention, the Lisuride was administered prior to oral administration of the alcohol to provide a reversal of the effects of the changes induced by the alcohol. In a second series of experiments the subjects were first administered the alcohol and only thereafter received the Lisuride. It was again established that the effects of the alcohol could be blocked by the Lisuride. The second study was carried out using the same basic method and materials but altered in that the Lisuride was administered after the subjects had already ingested sufficient alcohol so that changes in brain function has been induced. Both of the studies clearly established that Lisuride administered orally reverses the changes induced by alcohol.

The following example demonstrates physiological and behavioral blocking effects of Lisuride when administered after ingestion of alcohol.

EXAMPLE II

Material and Method

A. Demographic Data

Two male and one female psychologically and physically normal volunteers in the age range of 50-52 were included in this program. All volunteers were professionals and married.

B. Method

Each subject was given 50 cc. of 80 proof (40% alcohol) Vodka in 100 cc of orange juice, three times at half hour intervals. Subsequently, two male volunteers received again in half hour intervals 3 times 25 cc. Vodka (80 proof) (in 100 cc orange juice). The female volunteer could only drink 25 cc. of the Vodka before she got sick and the investigation had to be discontinued. All three volunteers received 50 mcg. of Lisuride orally approximately 5 minutes after the third dose (50 cc.) of alcohol.

Evaluations

Before the study and 20 minutes after alcohol administration psychomotor tests were conducted. Twenty five minutes after alcohol administration vital signs were examined and the side effects were evaluated based on the psychosomatic rating scale and 30 minutes after alcohol administration EEG was recorded.

As a psychomotor test, a task is given in which each subject was to move a pen from right to left in a spiral hole without touching the walls or the bottom. The time which was spent to move the pen from the point of the right side to the left side was registered as well as the errors (touching the walls and the bottom) and the time spent in the error.

EEG was recorded from right occipital to right ear lead for a period of 5 minutes. The subjects were sitting in comfortable chairs with their eyes closed. The EEG was recorded on the paper chart as well as on the magnetic tape (Ampex SP-700) and later the tapes were analyzed on line using digital computer period analysis programs with a mini-computer (IBM System 7).

RESULTS

Results of Individual Subjects

Subject T.I., project #1, Age: 51, Sex-Male

This subject showed the expected effects after the first and second dose of alcohol (each 50 cc. Vodka). These effects were most clearly seen in computerized EEG measurements and in CEEG profiles. Fifth mcg. of Lisuride administered orally blocked EEG changes induced by alcohol dramatically, although this subject subsequently received four more doses of alcohol. Psychomotor task performance improved with time, which probably may also be due to learning effect independent of alcohol or Lisuride effects. Also, the clinical side effects induced by alcohol were reduced by Lisuride administration.

Subject #2 (R.B.), Age: 49, Sex:Male

This subject showed obvious effects of alcohol clinically as well as in computerized EEG measurements. The alcohol-blocking effect of Lisuride was not as significant as subject #1.

Subject #3 (E.I.), Age:50, Sex:Female

This subject became ill during the experiment and therefore, the study could not be completed. The alcohol effect on brain function was similar to that seen in subject #1 and, to a lesser degree, in subject #2. Lisuride did not produce any significant blocking effect. However, it should be considered that the subject vomited after the Lisuride administration and therefore a full effect of Lisuride could not be expected.

GROUP RESPONSE

When the mean of three investigated subjects is computed, it was established that CEEG profiles of alcohol before Lisuride administration are different than those after Lisuride. For example, 26.6-40 cps activity was decreased by alcohol administration. However, after Lisuride despite of further administration of alcohol this activity increased instead of decreased and reached the values before alcohol administration.

According to this example, alcohol has systematic effects on behavior, in the computerized electroencephalogram and in psychomotor performance in these subjects. After the third drink of alcohol, administration of 50 mcg. Lisuride did significantly block the EEG effects of alcohol in one subject. In another subject this was not as significant, and in a third subject the effects could not be evaluated because she vomited after alcohol and Lisuride administration. However, when the mean data of the three subjects were evaluated, Lisuride, 50 mcg., orally administered, did reduce changes induced by alcohol. Despite subsequent alcohol administration, the CNS effects of alcohol were partially blocked.

Accordingly, Lisuride exhibits a blocking effect on acute alcohol induced CEEG changes and can be used therefore as a blocking agent for alcohol intoxication.

In its method of use aspect, this invention relates to the treatment of alcoholics and occassional drinkers for the purpose of blocking the clinical and physiological effects of alcohol. This has not only important implications in the treatment of chronic alcoholics but also in preventing the traffic accidents after social drinking. While the above studies relate to treatment of so called acute alcohol intoxication, results of preliminary experiments indicate that Lisuride administered for a period of 2-8 weeks and longer and in daily dosage of 25-75 mcg. is effective in the treatment of the chronic alcoholic i.e., in substantially lessening the otherwise behavioral and physiological changes observed in chronic alcoholism.

In medical practice, the drugs based on Lisuride according to the present invention can be administered orally and parenterally. The dosage to achieve the blocking effect is 25-75 mcg., preferably 50-75 mcg. and most preferably 50 mcg. The drug is administered about 1-3 preferably 2 hours before alcohol ingestion. Alternatively the drug can be administered from ½ - 3 hours preferably ½ to 2 hours after alcohol ingestion. In this case the dosage should be 75-150 mcg.

The formulation of the medicinal agents of this invention is accomplished in the conventional manner, by processing the Lisuride, together with the vehicles, diluents and flavor-accelerating substance, customary in galenic pharmacy, and then converting the composition into the desired forms of application, such as, for example, tablets dyagees, capsules and solutions suitable for oral administration and ampulles suitable for parenteral administration.

I claim:

1. A method for blocking and for delaying alcohol induced computer EEG changes which comprises administering orally to a subject prior to the ingestion by that subject of alcohol, an amount of Lisuride effective to block the behavioral and physiological effects of the alcohol and thereafter administering orally to that subject said alcohol.

2. A method according to claim 1, wherein the amount of Lisuride administered is 1–150 mcg.

3. A method according to claim 1, wherein the Lisuride is administered from 1 to 3 hours prior to ingestion of said alcohol.

4. A method according to claim 1, wherein the Lisuride is administered for period of 2–8 weeks or longer in daily dosages of 25–75 mcg.

5. A method according to claim 1, wherein the Lisuride is administered 1 to 2 hours prior to ingestion of alcohol.

6. A method according to claim 1, wherein the Lisuride is administered in an amount of 50 mcg.

7. A method according to claim 1, wherein the Lisuride is administered in an amount of 100 mcg.

8. A method for blocking and for delaying alcohol induced computer EEG changes which comprises administering orally to a subject alcohol and subsequent to the ingestion by that subject of alcohol, administering orally an amount of Lisuride effective to block the behavioral and physiological effects of the alcohol.

9. A method according to claim 8, wherein the Lisuride is administered from 1 to 3 hours subsequent to the ingestion of alcohol.

10. A method according to claim 8, wherein the amount of Lisuride administered is 1–150 mcg.

* * * * *